United States Patent [19]

Tomcufcik et al.

[11] 4,377,589
[45] Mar. 22, 1983

[54] SUBSTITUTED 2-ALKYLIMINO-3-ALKYL-4-BENZHYDRYL-4-THIAZOLIDINOLS

[75] Inventors: Andrew S. Tomcufcik, Old Tappan; William B. Wright, Jr., Woodcliff Lake, both of N.J.; Joseph W. Marsico, Jr., Pearl River, N.Y.

[73] Assignee: American Cyanamid Company, Stamford, Conn.

[21] Appl. No.: 252,529

[22] Filed: Apr. 9, 1981

[51] Int. Cl.³ ............... C07D 277/04; A61K 31/425
[52] U.S. Cl. ............................................. 424/270; 548/184
[58] Field of Search ........................ 424/270; 548/184

[56] References Cited

U.S. PATENT DOCUMENTS 2,837,529  6/1958  Winthrop ........................ 548/184
4,156,735  5/1979  Lang et al. ...................... 548/184

Primary Examiner—Nicholas S. Rizzo
Attorney, Agent, or Firm—Edward A. Conroy, Jr.

[57] ABSTRACT

This disclosure describes substituted 2-alkylimino-3-alkyl-4-benzhydryl-4-thiazolidinols which are useful as diuretic agents.

8 Claims, No Drawings

SUBSTITUTED 2-ALKYLIMINO-3-ALKYL-4-BENZHYDRYL-4-THIAZOLIDINOLS

BRIEF SUMMARY OF THE INVENTION

This invention relates to new organic compounds and, more particularly, is concerned with novel substituted 2-alkylimino-3-alkyl-4-benzhydryl-4-thiazolidinols which may be represented by the following structural formula:

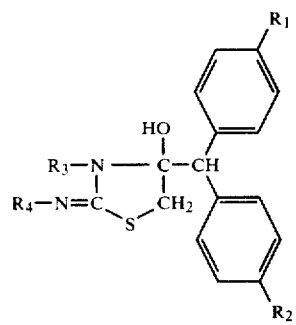

wherein $R_1$ is hydrogen, fluoro or chloro; $R_2$ is hydrogen, fluoro or chloro; $R_3$ is alkyl having from one to four carbon atoms; and $R_4$ is alkyl having from one to four carbon atoms; as well as the pharmaceutically acceptable acid-addition salts thereof.

The invention is also concerned with pharmaceutical compositions comprising these new compounds as well as methods for inducing diuresis employing these compounds and, further, to methods for their preparation.

DETAILED DESCRIPTION OF THE INVENTION

The novel compounds of the present invention are obtainable as white to light tan crystalline materials having characteristic melting points and absorption spectra. The free bases are, in general, relatively insoluble in water but soluble in most organic solvents such as lower alkanols, benzene, chloroform, acetone, etc. The organic bases of this invention form acid-addition salts with a variety of pharmacologically acceptable organic and inorganic salt-forming reagents. Thus, acid-addition salts, formed by admixture of the organic free base with an acid, suitably in a neutral solvent, are formed with such acids as sulfuric, phosphoric, hydrochloride, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

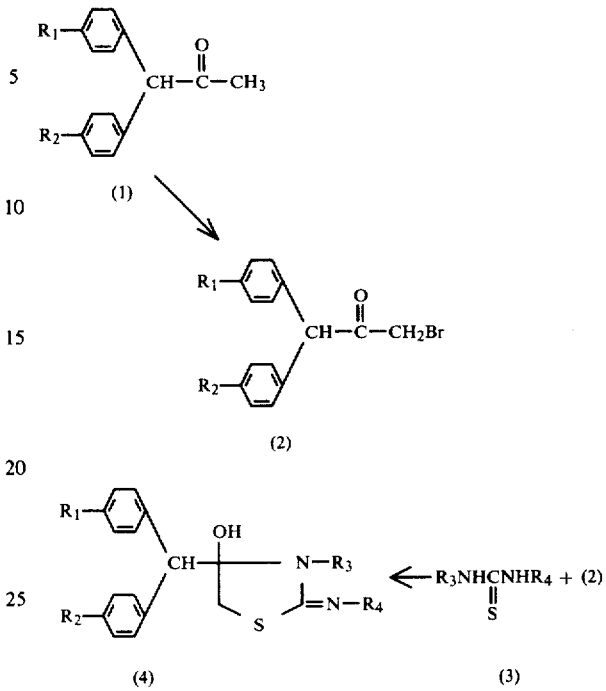

wherein $R_1$, $R_2$, $R_3$ and $R_4$ are as hereinabove defined. In accordance with the above reaction scheme, a 1,1-diaryl-2-propanone (1) is dissolved in glacial acetic acid and treated with one equivalent of bromine at 50°–80° C. for 30 minutes to 4 hours giving the 3-bromo-1,1-diaryl-2-propanone (2). Reaction of (2) with a 1,3-dialkyl-2-thiourea (3) in a solvent such as acetone at room temperature for 1–24 hours gives the products (4).

Procedures for the preparation of the 1,1-diaryl-2-propanones (1) are well known and may be found in such references as: M. J. Hatch and D. J. Cram, J.A.C.S. 75, 38 (1953); E. J. Cragoe, Jr., A. M. Pietruszkiewicz and C. M. Robb, J. Org. Chem. 23, 971 (1958); and E. M. Schultz, U.S. Pat. No. 2,703,329. It is also possible to prepare the 3-bromo-1,1-diaryl-2-propanones (1) by other methods. For example, the Arndt-Eistert synthesis of an acid chloride with diazomethane and hydrobromic acid [G. W. Wheland, Advanced Organic Chemistry, John Wiley and Sons, Inc., 2nd Edition, p. 462 (1948)].

The new compounds of the present invention possess diuretic activity in warm-blooded animals as established when tested by the method of P. S. Chan and D. Poorvin, Clinical And Experimental Hypertension, 1 (6), 817–830 (1979), Sequential Method for Combined Screening Antihypertensive and Diuretic Agents in the Same Spontaneously Hypertensive Rat.

Basically this test uses male, 8 week old, spontaneously hypertensive rats of the Okamoto strain weighing about 300 g. One rat is dosed by gavage with the test compound at 100 mg./kg. of body weight with 0.9% sodium chloride loading at 25 ml./kg. of body weight at zero hour. The test compound is suspended in 2% preboiled starch at 50 mg./ml. The rat is placed in a metabolism cage and the 0–5 hour urine is collected. The urinary sodium, potassium and chloride content are determined by the Technicon Autoanalyzer; method N-20 for sodium and potassium and method N-5b for chloride. Based on the data obtained and using the three-stage "sequential probability ratio test", statistical method, the criteria for determining if a test compound is considered active are as follows:

Test I: If the urinary sodium is ≧1.21 mEq the compound is active. If the urinary sodium is between 1.21–0.93, a second rat is tested.

Test II: If the average urinary sodium of the two rats is >1.16 mEq the compound is considered active. If the average urinary sodium is between 1.16–1.01 a third rat is tested.

Test III: If the average urinary sodium of the three rats is ≧1.10 the compound is active.

The results of this test on representative compounds of the present invention appear in Table I.

TABLE I

| Compound | Urinary Values in mEq/5 hours | | |
|---|---|---|---|
| | Volume (ml.) | Na+ | K+ |
| 4-Diphenylmethyl-3-methyl-2-methylimino-4-thiazolidinol, hydrobromide | 14.0 | 1.43 | 0.67 |
| 4-Diphenylmethyl-3-ethyl-2-ethylimino-4-thiazolidinol, hydrobromide | 12.8 | 1.52 | 0.57 |
| 4-[p-Chloro-α-(p-fluorophenyl)benzyl]-3-methyl-2-methylimino-4-thiazolidinol, hydrobromide | 11.5 | 1.50 | 0.83 |
| 2-(tert.-Butylimino)-4-diphenylmethyl-3-methyl-4-thiazolidinol, hydrobromide | 14.5 | 1.53 | 0.54 |
| 4-(p-Chloro-α-phenylbenzyl)-3-methyl-2-methylimino-4-thiazolidinol, hydrobromide | 10.7 | 1.28 | 0.79 |
| 4-(p-Fluoro-α-phenylbenzyl)-3-methyl-2-methylimino-4-thiazolidinol, hydrobromide | 12.5 | 1.21 | 0.93 |
| 4-Diphenylmethyl-3-methyl-2-methylimino-4-thiazolidinol | 11.3 | 1.33 | 0.37 |

The active compounds of the present invention are effective in inducing diuresis in warm-blooded animals when administered in amounts ranging from about 5 gm. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 g. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain the following: A binder such as gum tragacanth, acacia, corn starch or gelatin; excipients such as dicalcium phosphate; a disintegraing agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, the active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganism such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following specific examples.

EXAMPLE 1

3-Bromo-1,1-diphenyl-2-propanone

The subject compound is prepared essentially by the procedure of C. L. Stevens and C. T. Lenh, J. Org. Chem. 19, 538 (1954).

To a stirred solution of 42.0 g. of 1,1-diphenyl-2-propanone in 150 ml. of glacial acetic acid at 60°–70° C., is added dropwise, over 45 minutes, a solution of 32.0 of bromine in 25 ml. of glacial acetic acid. The mixture is then stirred for one hour at 60°–70° C. The mixture is poured into 500 ml. of ice, allowed to stand in a refrigerator overnight, and the solid is collected by filtration, washed with water and ice-cold isopropanol, and recrystallized from isopropanol, giving 29.0 of the desired product as light pink crystals, m.p. 62°-64° C.

When the procedure of Example 1 is carried out using other diaryl ketones instead of 1,1-diphenyl-2-propanone, the brominated diaryl ketones of Examples 2-5 (listed in tabular form) are derived.

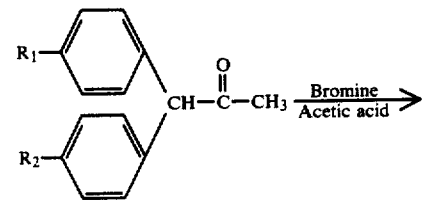

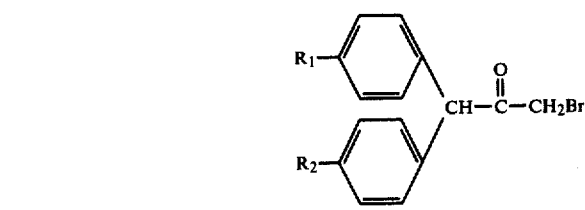

| Ex. | 1,1-Diaryl ketone $R_1$ | $R_2$ | Brominated 1,1-diaryl ketone intermediate | M.P. °C. |
|---|---|---|---|---|
| 2 | p-Cl | p-F | 3-Bromo-1-(p-chlorophenyl)-1-(p-fluorophenyl)-2-propanone | Oil |
| 3 | p-F | p-F | 3-Bromo-1,1-bis(p-fluorophenyl)-2-propanone | Oil |
| 4 | p-Cl | H | 3-Bromo-1-(p-chlorophenyl)-1-phenyl-2-propanone | Oil |
| 5 | p-F | H | 3-Bromo-1-(p-fluorophenyl)-1-phenyl-2-propanone | Oil |

EXAMPLE 6

4-Diphenylmethyl-3-methyl-2-methylimino-4-thiazolidinol hydrobromide

To a filtered solution of 1.04 g. of 1,3-dimethyl-2-thiourea in 25 ml. of acetone is added a filtered solution of 2.73 g. of 3-bromo-1,-diphenyl-2-propanone (Example 1) in 25 ml. of acetone. The mixture is allowed to stand several hours at room temperature and the solid is recovered by filtration, washed with acetone and dried in vacuo, giving 3.38 g. of the desired product as light tan crystals, m.p. 245°-247° C. (dec.).

When the above procedure is carried out using the intermediate brominated diaryl ketones of Examples 2-5 instead of 3-bromo-1,1-diphenyl-2-propanone, the final products of Examples 7-10 (listed in tabular form below) are obtained.

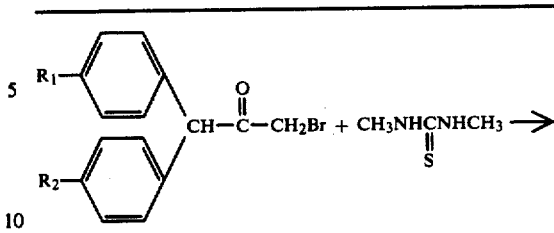

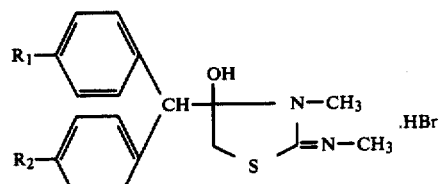

| Ex. | Intermediate Ex. No. | Product | M.P. °C. |
|---|---|---|---|
| 7 | 3 | 4-[bis(p-Fluorophenyl)methyl]-3-methyl-2-methylimino-4-thiazolidinol hydrobromide | 226-228 |
| 8 | 2 | 4-[p-Chloro-α-(p-fluorophenyl)benzyl]-3-methyl-2-methylimino-4-thiazolidinol hydrobromide | 252-255 |
| 9 | 4 | 4-(p-Chloro-α-phenylbenzyl)-3-methyl-2-methyl-imino-4-thiazolidinol hydrobromide | 253-255 |
| 10 | 5 | 4-(p-Fluoro-α-phenylbenzyl)-3-methyl-2-methyl-imino-4-thiazolidinol hydrobromide | 206-208 (dec.) |

EXAMPLE 11

4-Diphenylmethyl-3-methyl-2-methylimino-4-thiazolidinol

To a solution of 7.17 g. of 3-methyl-2-methylimino-4-diphenylmethyl-4-thiazolidinol hydrobromide (Example 6) in 300 ml. of methanol:water (2.1 v/v) is added, with stirring, 1.8 ml. of 10 N sodium hydroxide. The mixture is chilled, producing a gum which crystallizes on warming to room temperature. These crystals are collected by filtration, washed with methanol:water (2:1) and dried, giving 2.76 g. of the desired product, m.p. 133°-136° C.

EXAMPLE 12

4-Diphenylmethyl-3-methyl-2-methylimino-4-thiazolidinol hydrochloride

To a warm solution of 4.80 g. of 3-methyl-2-methylimino-4-diphenylmethyl-4-thiazolidinol (Example 11) in 50 ml. of ethanol is added 15 ml. of 3.48 N ethanolic hydrochloric acid. The solution is diluted to 200 ml. with ethanol and allowed to stand. The crystals are recovered by filtration, washed with ethanol and dried, giving 4.59 g. of the desired product, m.p. 252°-254° C. (dec.).

EXAMPLE 13

2-(tert.-Butylimino)-4-diphenylmethyl-3-methyl-4-thiazolidinol hydrobromide

A 1.48 g. portion of 1-tert.-butyl-3-methyl-2-thiourea in 75 ml. of acetone is treated with a clarified solution of 2.89 g. of 3-bromo-1,1-diphenyl-2-propanone in 75 ml. of acetone. The mixture is stirred at room temperature for 17 hours. The solid is collected by filtration, washed with acetone and dried at 60° C. in vacuo, giving 2.8 g. of the desired product, m.p. 170°–172° C. (dec.).

EXAMPLE 14

4-Diphenylmethyl-3-ethyl-2-ethylimino-4-thiazolidinol hydrobromide

To a filtered solution of 1.32 g. of 1,3-diethyl-2-thiourea in 25 ml. of acetone is added a filtered solution of 3-bromo-1,1-diphenyl-2-propanone in 25 ml. of acetone. The mixture is allowed to stand, then the solid is collected by filtration, washed with acetone and dried in vacuo, giving 3.73 g. of the desired product, m.p. 174°–176° C. (dec.).

We claim:

1. A compound selected from the group consisting of the formula:

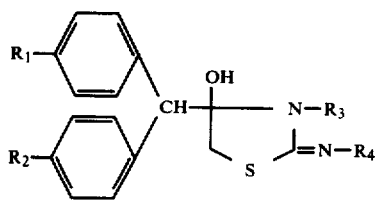

wherein $R_1$ is hydrogen, fluoro or chloro, $R_2$ is hydrogen, fluoro or chloro $R_3$ is alkyl having up to 4 carbon atoms, and $R_4$ is alkyl having up to 4 carbon atoms; and the pharmacologically acceptable acid-addition salts thereof.

2. The compound according to claim 1 wherein $R_1$ is hydrogen, $R_2$ is chloro, $R_3$ is ethyl, and $R_4$ is n-propyl; 4-(p-chloro-α-phenylbenzyl)-3-ethyl-2-n-propylimino-4-thiazolidinol.

3. The compound according to claim 1 wherein $R_1$ is hydrogen, $R_2$ is fluoro, $R_3$ is sec.-butyl, and $R_4$ is methyl; 4-(p-fluoro-α-phenylbenzyl)-3-sec.-butyl-2-methylimino-4-thiazolidinol.

4. The compound according to claim 1 wherein $R_1$ and $R_2$ are both chloro, $R_3$ is n-butyl, and $R_4$ is methyl; 4-[bis(p-chlorophenyl)methyl]-3-n-butyl-2-methylimino-4-thiazolidinol.

5. The compound according to claim 1 wherein $R_1$ and $R_2$ are both fluoro, $R_3$ is ethyl, and $R_4$ is isobutyl; 4-[bis(p-fluorophenyl)methyl]-3-ethyl-2-isobutylimino-4-thiazolidionol.

6. The compound according to claim 1 wherein $R_1$ and $R_2$ are both chloro, $R_3$ is isopropyl, and $R_4$ is methyl; 4-[bis(p-chlorophenyl)methyl]-3-isopropyl-2-methylimino-4-thiazolidinol.

7. The compound according to claim 1 wherein $R_1$ is fluoro, $R_2$ is chloro, $R_3$ and $R_4$ are both isopropyl, and as the tartaric acid salts; 4-[p-chloro-α-(p-fluorophenyl)benzyl]-3-isopropyl-2-isopropylimino-4-thiazolidinol tartrate.

8. The method of inducing diuresis in a mammal which comprises administering to said mammal a diuretic effective amount of a compound of the formula:

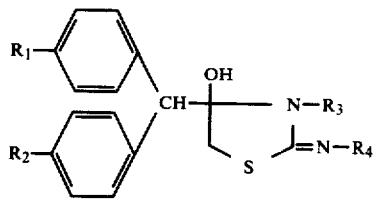

wherein $R_1$ and $R_2$ may be the same or different and are hydrogen, fluoro or chloro and $R_3$ and $R_4$ may be the same or different and are alkyl having up to 4 carbon atoms; or the pharmaceutically acceptable acid-addition salts thereof.

* * * * *